(12) United States Patent
Dimanshteyn (10) Patent No.: US 7,824,904 B1
(45) Date of Patent: Nov. 2, 2010

(54) PHOTOBIOREACTORS FOR PRODUCTION OF ALGAE AND METHODS THEREFOR

(76) Inventor: Felix Dimanshteyn, 675 Mountain Rd., West Hartford, CT (US) 06117

(*) Notice: Subject to any disclaimer, the term of this patent is extended or adjusted under 35 U.S.C. 154(b) by 190 days.

(21) Appl. No.: 11/999,338

(22) Filed: Dec. 5, 2007

Related U.S. Application Data (60) Provisional application No. 60/874,068, filed on Dec. 11, 2006.

(51) Int. Cl.
*C12M 1/00* (2006.01)
*C12M 3/00* (2006.01)

(52) U.S. Cl. .................. 435/292.1; 47/1.4; 362/101

(58) Field of Classification Search ............ 435/292.1, 435/257.1, 289.1; 250/504 R; 47/1.4; 362/563, 362/551, 101; 385/900
See application file for complete search history.

(56) References Cited

U.S. PATENT DOCUMENTS

| | | | | |
|---|---|---|---|---|
| 3,986,297 A | * | 10/1976 | Ichimura et al. | ......... 435/292.1 |
| 4,952,511 A | | 8/1990 | Radmer | |
| 5,027,550 A | * | 7/1991 | Mori | ............... 47/1.4 |
| 5,031,986 A | * | 7/1991 | Mori | ............... 385/25 |
| 5,104,803 A | | 4/1992 | Delente | |
| 5,614,378 A | | 3/1997 | Yang et al. | |
| 5,846,816 A | | 12/1998 | Forth | |
| 6,602,703 B2 | | 8/2003 | Dutil | |
| 6,603,069 B1 | | 8/2003 | Muhs | |
| 2004/0256857 A1 | * | 12/2004 | Bailey, III | ............ 290/43 |
| 2005/0026262 A1 | * | 2/2005 | Yoshitani et al. | ............ 435/167 |
| 2005/0260553 A1 | * | 11/2005 | Berzin | ............ 435/3 |
| 2006/0223155 A1 | * | 10/2006 | Streeter | ............ 435/173.8 |
| 2007/0151844 A1 | * | 7/2007 | Wilson et al. | ............ 204/230.2 |
| 2007/0264708 A1 | * | 11/2007 | Bayless et al. | ............ 435/292.1 |
| 2009/0029445 A1 | * | 1/2009 | Eckelberry et al. | ........ 435/257.1 |
| 2010/0034050 A1 | * | 2/2010 | Erb et al. | ............ 366/342 |

* cited by examiner

*Primary Examiner*—William H Beisner
*Assistant Examiner*—Danielle Henkel (57) ABSTRACT

The present invention is directed to a photobioreactor comprising: (a) a tank for containing a liquid microbial culture; (b) a rotating mixing system contained within the tank, the rotating mixing system comprising one or more motors, and one or more shafts connected to the one or more motors, and a plurality of mixing blades attached to the one or more shafts, wherein the mixing blades are capable of mixing the microbial culture throughout the volume of the tank; (c) a lighting system, comprising a light source located outside the tank; a light emitting device mounted on the blades; and a conduit that transfers light from the light source to the light emitting device, wherein the lighting system is capable of providing sufficient light for growth of the microbial culture throughout the volume of the tank. The rotating system may be replaced with an oscillating system, and either system can be mounted on a moveable raceway.

26 Claims, 3 Drawing Sheets

PHOTOBIOREACTORS FOR PRODUCTION OF ALGAE AND METHODS THEREFOR

CROSS-REFERENCE TO RELATED APPLICATIONS

This application claims the benefit of U.S. Provisional Patent Application Ser. No. 60/874,068 filed Dec. 11, 2006. This provisional application is herein incorporated by reference in its entirety.

BACKGROUND OF THE INVENTION

1. Field of the Invention

The present invention is directed to photobioreactors and their use in the production of biomass, and more particularly to photobioreactors with rotating and/or oscillating lighting and mixing systems that provide delivery of light to all areas of the photobioreactors.

2. Description of the Related Art

Algae have been cultivated artificially for such diverse purposes as the production of food for animals and humans, the treatment of sewage and waste waters, and the accumulation of radioactive wastes. More recently, algal cultures have been used for the production of enzymes having industrial and research applications and for producing oils and other materials having value as fuels such as biodiesel fuel or ethanol. However, production of biodiesel and ethanol fuels can be expensive and inefficient processes. It would be desirable to increase the efficiency of production of these materials in order to meet rising world demand.

Photobioreactors are known in the art, and are generally used for the production of biomass. Photobioreactors generally consist of a vessel containing a liquid medium that is exposed to a light source. However, the configuration of the photobioreactor often prevents the light from penetrating more than a few centimeters from the surface of the liquid. This problem reduces the efficiency of the photobioreactor, and was recognized in "Solar Lightning for Growth of Algae in a Photobioreactor" published by the Oak Ridge National Lab and Ohio University:

Light delivery and distribution is the principle obstacle to using commercial-scale photobioreactors for algae production. In horizontal cultivator systems, light penetrates the suspension only to 5 cm leaving most of the algae in darkness. The top layer of algae requires only about $\frac{1}{10}$th the intensity of full sunlight to maximize growth, so the remaining sunlight is wasted.

According to Mario R. Tredici: "Outdoors, under full sunlight, the photosynthetic efficiency drops to one tenth-one fifth of the values observed at low irradiances. The major causes for this inefficiency are the light saturation effect (LSE) and photoinhibition, phenomena that strongly limit the grows of microalgae in out door culture, although these because of the high cell density, are light-limited. The main problem is that photosynthetic apparatus of phototrophs saturates at low irradiances (typically from $\frac{1}{20}$ to $\frac{1}{10}$ of full sunlight) and that, at irradiances above saturation, the absorbed photons are used inefficiently and may cause cell injury. Several strategies to overcome the LSE and photoinhibition have been proposed, based on engineering (light dilution, ultra high cell density culture, high turbulence), physiologic (photoacclimation, nutrient deprivation) or genetic . . . ." (Tredici M. R. (2004) Mass production of microalgae: photobioreactors. In Richmond A (ed.), Handbook of Microalgae Culture. Blackwell Publishing, Oxford (UK), pp 178-214.

As described in Healthy Algae, Fraunhofer Magazine, January 2002, "Algae are a very undemanding life form— they only need water, $CO_2$, nutrients and sunlight. However, providing sufficient sunlight can be a problem in large scale facilities. "As the algae at the surface absorb the light, it does not penetrate to a depth of more than a few millimeters. The organism inside the unit gets no light and cannot grow," explains Walter Troesch, who has been cultivating algae for years. "This is the reason why there are only a few Algae production units dotted around the world. One of the problems with growing algae in any kind of pond is that only in the top $\frac{1}{4}$" or so of the pond receives sufficient solar radiation for the algae to grow. In effect, this means that the ability of a pond to grow algae is limited by its surface area, not by its volume."

Algae are a useful organism. Algae contain fat, carbohydrates, and protein. Some of the micro-algae contain up to 60% fat. Once the fat is 'harvested'—some 70% can be harvested by pressing, and what remains becomes a good animal feed or can be processed to produce ethanol, according to "Cultivating Algae for Liquid Fuel Production" by Thomas F. Riesing, Ph.D.

Closed photobioreactors are known for use in the production of biomass. See, for example, U.S. Pat. No. 5,151,347 to Delente et al. One type of photobioreactor is a tubular type, such as the industrial tubular photobioreactor that was established near Wolfsburg, Germany in 2000. This particular tubular photobioreactor has a total tube length of approximately 500,000 meters, and a total volume of approximately 700 cubic meters. Total annual production of biomass from this photobioreactor is estimated to be approximately 130-150 tons of dry biomass in an area of approximately 10,000 square meters (O. Pulz, IGV Institute for Cereal Processing, Arthur-Scheunert-Allee 40/41, 14558 Bernholz-Rehbrucke, Germany). Another type of closed photobioreactor is a tank with immersed light-emitting tubes. These types of photobioreactors were considered in patents bellow.

Approaches have been described to increase the efficiency of the photobioreactors by using artificial light sources. For example, U.S. Pat. No. 6,602,703 discloses a photobioreactor having light-emitting tubes mounted within the container. U.S. Pat. No. 5,104,803 discloses a photobioreactor for the cultivation of photosynthetic microorganisms having at least one light bank substantially totally immersible in the liquid microbial culture. U.S. Pat. No. 5,614,378 discloses a photobioreactor system that includes a fiber optic based optical transmission system that illuminates the reactor internally and includes a light source which is external to the reactor.

In addition, one problem with available photobioreactors is that any liquid microbial culture will receive light only near the top of the reactor, or near the lighting system. As the culture becomes more dense, light has difficulty penetrating this dense microbial culture. The result is that only the lighted space is effective for growing the microbial culture, and this leads to inefficiencies in the production system.

Although many photobioreactors have been proposed in the prior art, there is still a need for an improved photobioreactor using artificial light so that the efficiency of these devices may be increased. The present invention is believed to be an answer to that need.

SUMMARY OF THE INVENTION

In one embodiment, the present invention is directed to a photobioreactor comprising:

(a) a tank for containing a liquid microbial culture;

(b) a rotating mixing system comprising one or more motors, and one or more shafts connected to the one or more motors, and a plurality of mixing blades attached to the one or more shafts, wherein the mixing blades are capable of mixing the microbial culture throughout the volume of the tank;

(c) a lighting system, comprising
  a light source located outside the tank;
  a light emitting device mounted on the blades or rotating mixing system; and
  a conduit that transfers light from the light source to the light emitting device, wherein the lighting system is capable of providing sufficient light for growth of the microbial culture throughout the volume of the tank.

In another embodiment, the present invention is directed to a photobioreactor comprising:
  (a) a tank for containing a liquid microbial culture;
  (b) a rotating light-emitting mixing system comprising one or more motors, and one or more shafts connected to the one or more motors, and a lighting system comprising:
    (1) a light source located outside the tank;
    (2) one or more light-emitting blades attached to the one or more shafts, wherein the light-emitting mixing blades are capable of mixing the microbial culture throughout the volume of the tank; and
    (3) a conduit that transfers light from the light source to the light emitting blades, wherein the lighting system is capable of providing sufficient light for growth of the microbial culture throughout the volume of the tank.

In another embodiment, the present invention is directed to a photobioreactor comprising:
  (a) a tank for containing a liquid microbial culture;
  (b) an oscillating mixing system comprising a frame system comprising fixed frames and oscillating frames, one or more oscillating movers attached to the fixed frames and the moving frames and providing oscillation, mixing blades attached to the oscillating frames, wherein the mixing blades are capable of mixing the microbial culture throughout the volume of the tank;
  (c) a lighting system, comprising
    a light source located outside the tank;
    a light emitting device mounted on the blades or on the oscillating mixing system; and
    a conduit that transfers light from the light source to the light emitting device; wherein the lighting system is capable of providing sufficient light for growth of the microbial culture throughout the volume of the tank.

In another embodiment, the present invention is directed to a photobioreactor comprising:
  (a) a tank for containing a liquid microbial culture;
  (b) an oscillating light-emitting mixing system comprising a frame system comprising fixed frames and oscillating frames, one or more oscillating movers attached to the fixed frames and the oscillating frames and providing oscillation, and a lighting system comprising:
    (1) a light source located outside the tank;
    (2) one or more light-emitting blades attached to the oscillating frames, wherein the light-emitting mixing blades are capable of mixing the microbial culture throughout the volume of the tank; and
    (3) a conduit that transfers light from the light source to the light emitting blades; wherein the lighting system is capable of providing sufficient light for growth of the microbial culture throughout the volume of the tank.

In another embodiment, the present invention is directed to a photobioreactor, comprising:
  a body of water containing a liquid microbial culture;
  a mobile framework which moves through all areas of the body of water; and
  a rotating lighting and mixing system as described above, or the oscillating lighting and mixing system described above, attached to the mobile frame.

The above photobioreactors may also include a carbon dioxide generating system comprising: a furnace for burning fuel; a system to transfer carbon dioxide to said photobioreactor; and a system to remove excess oxygen from said photobioreactor.

BRIEF DESCRIPTION OF THE DRAWINGS

The invention will be better understood when taken in conjunction with the following drawings in which.

It is to be understood that the above drawings are representative embodiments and are not to be construed as limiting on the present invention.

DETAILED DESCRIPTION OF THE INVENTION

The present invention is directed to photobioreactors and methods of production bio-diesel fuel, ethanol and protein for food using these photobioreactors. As indicated above, photobioreactors have previously been used in the production of algae. Photobioreactors offer the advantage of providing ample space and controlled conditions for growing microorganisms such as algae. With a photobioreactor, it is possible to closely control the supply of water, nutrients including sewage, carbon dioxide, temperature, pH, salinity, and the like, that the microorganisms use for growth. Photobioreactors also provide for reduced contamination of the microorganisms.

A major disadvantage of current photobioreactors is their inability to provide sufficient lighting necessary to optimize growth of the microorganisms. Conventional lighting sources provided outside the photobioreactor only penetrate a short distance into the interior of the photobioreactor vessel. This short penetration allows for only a small part of the tank to have the necessary amount of light, and therefore only a small fraction of the microorganisms are capable of metabolizing at an optimum level. Further, current implementation of lighting systems inside photobioreactors are primarily stationary, and thus only provide a light source to the microorganisms closest to the light. In addition, the microorganisms surround the stationary lights and block light from accessing other areas of the photobioreactor.

To overcome this disadvantage, the present invention is a photobioreactor with a light source provided on the inside of the reaction vessel in the form of rotating and/or oscillating lighting and mixing system. This system allows for distribution of any amount of light and nutrients and carbon dioxide to any and all areas of the photobioreactor, which in turn provides that each microbial cell will receive as much light and nutrients as necessary for optimum growth. As defined herein, the term "oscillating" means any regular, repetitive motion that results in mixing, such as a back and forth motion, or a continuous circular motion. Additionally, in combination with vigorous mixing, the interior light source provides optimum amount of light to the microorganisms and results in a photobioreactor with improved efficiency. Due to the large efficiencies provided, the photobioreactor of the present invention has the capability to reduce the required space for growing algae by 10 to 100 times or more.

Figure 1:
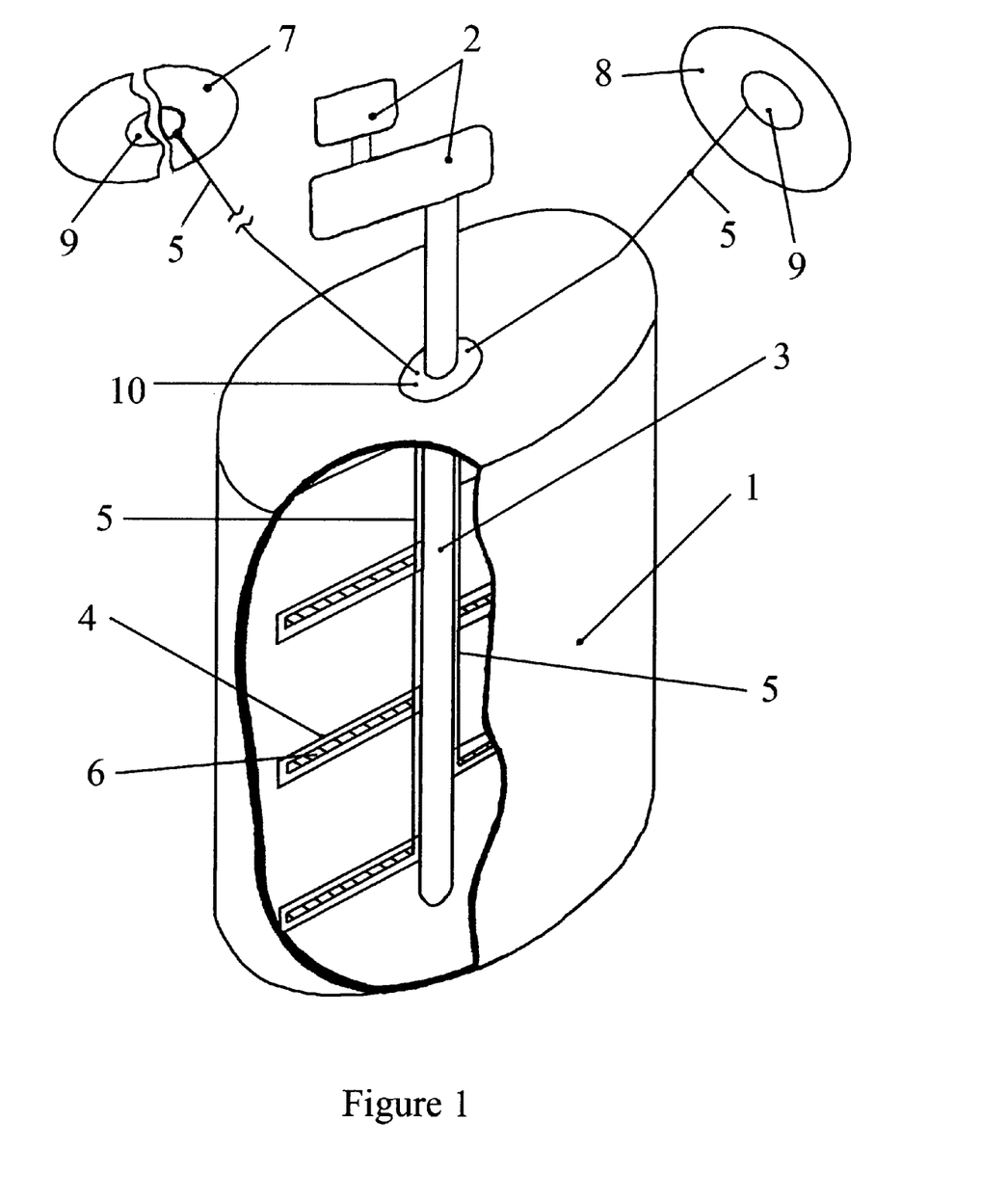
FIG. 1 is a schematic diagram of one embodiment of the photobioreactor of the present invention.

The photobioreactor of the present invention is shown in FIG. 1. As shown in FIG. 1, in one embodiment of the present invention, the photobioreactor includes a tank 1 for containing a liquid microbial culture, and a mixing system comprising a motor and gearbox 2 connected to a shaft 3 that includes blades 4 and lighting system. The terms "biomass", "microbial", and "microorganism" as used herein includes all organisms capable of photosynthetic growth such as plant cells and microorganisms (including algae and euglena) in unicellular or multicellular form that are capable of growth in a liquid phase. The term may also include organisms modified artificially or by gene manipulation. In one embodiment, algae are the preferred microbial culture because they form an easily manipulated biomass. The microbial culture may be provided with any source of nutrients known in the art, including premade feeds, sewage, and carbon dioxide.

The tank 1 of the photobioreactor may be any suitable vessel used in the bioprocessing art, such as stainless steel, plastic, glass, cement, and the like. Glass and transparent plastic vessels offer an advantage in that natural sunlight can penetrate directly inside the photobioreactor. In alternative embodiments, the tank may be an open body of liquid, such as a pool, pond, or raceway cultivator, or may be closed tanks such as a cylindrical tower or tank, or an underground tank. The tank may also be closed or open. The tank is of a size sufficient to hold a desired amount of liquid microbial culture.

Figure 2:
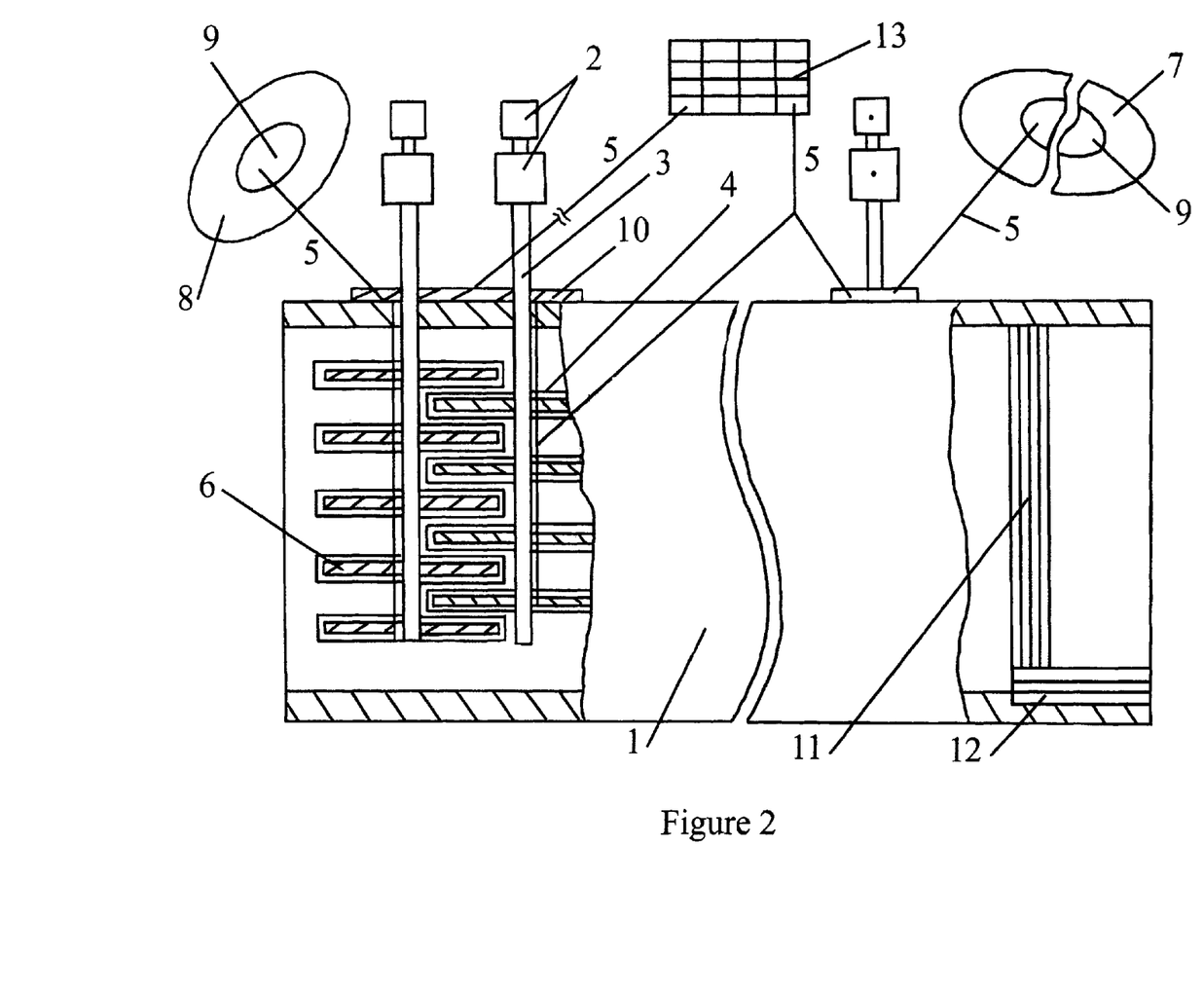
FIG. 2 is a schematic diagram of another embodiment of the photobioreactor of the present invention.
Figure 3:
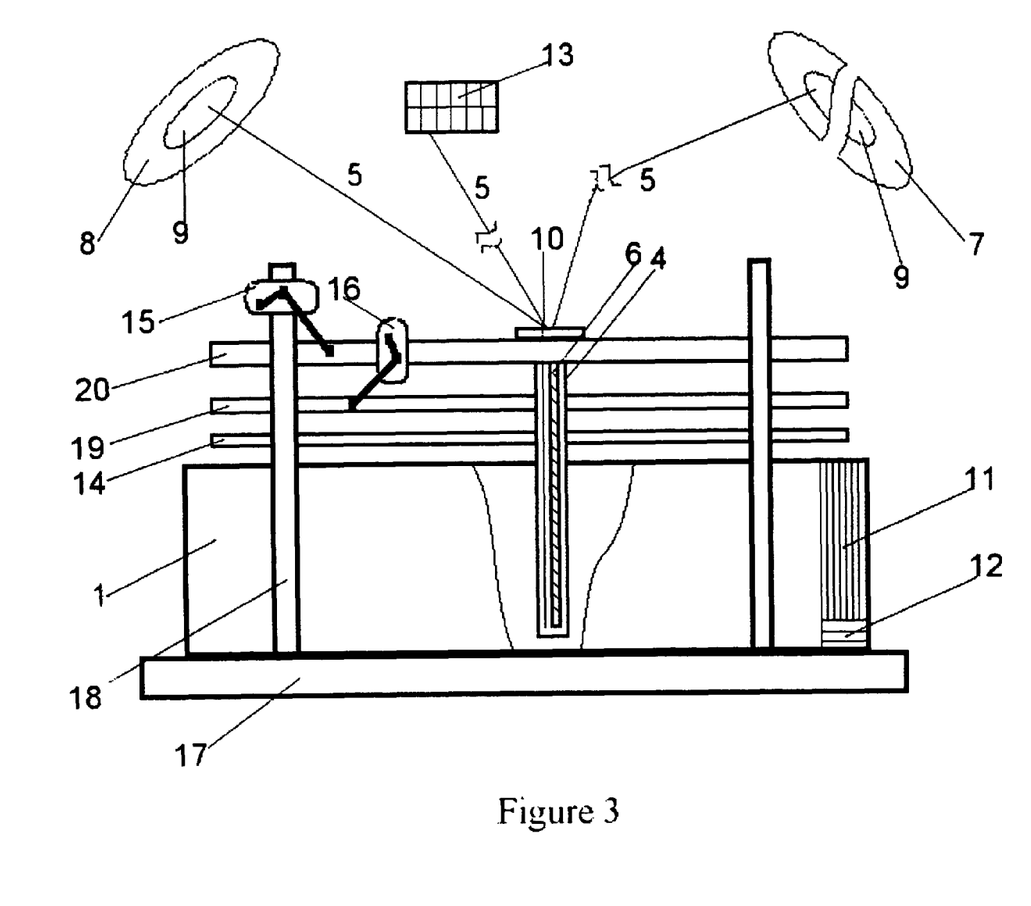
FIG. 3 is a schematic diagram of another embodiment of the photobioreactor of the present invention.

In an alternative embodiment, the tank can be constructed as continuous photobioreactor as shown in FIGS. 2 and 3 where a liquid microbial culture such as algae should grow in the continuous photobioreactor for certain amount of time for certain species before end of their life cycle, or the desired level of growth is achieved. This time will determine speed of the movement of algae and length of the continuous photobioreactor. In the same time amount of growing Algae will be determine by orifice of the tank and speed of movement of a liquid microbial culture. The tank can be made as a pipe or in a straight, U-shaped, or spiral format, and can be any shape such as round, square, or rectangular. The tank can be constructed in a modular design, such that sections of tank are connected together to form a tank with a total desired volume. The volume of the tank can be pre-selected by the user, and may be achieved in several ways. In one embodiment, the tank is assembled in sections where the beginning of one tank connects to the end of another until desired length is achieved. In another embodiment, the tanks can be placed one on the top of another and/or can be placed next to each other.

The microbial culture should be provided with a source of required nutrients known in the art, including premade feeds, sewage, and carbon dioxide. As defined herein, the term "nutrients" refers to the specific metabolic requirements needed to grow and sustain a microbial or algal culture, including the raw sources of those requirements. Carbon dioxide can be obtained from different sources such as power plants, from burning coal, gasoline and diesel, cellulose and the like. Processes of obtaining carbon dioxide for the photobioreactors of the present invention are described in more detail below.

A rotating and/or oscillating lighting and mixing system is contained within the tank for mixing the microbial culture and for delivering light to each point in the tank. The rotating mixing system comprises one or more motors and one or more gearboxes 2 that are in mechanical communication with a mixing device having a shaft 3 and blades 4 as shown in FIGS. 1 and 2. The oscillating mixing system (see FIG. 3) also comprises at least one motor and gearbox 15, 16 that is in mechanical communication with a mixing device which consists of oscillating frame system with blades. This oscillating frame system can consist of several frames; some of them can oscillate in different directions, for example, some of them can oscillate back and forward, the others can oscillate up and down. The motor may be of any type, for example electric or pneumatic motors, or any pneumatic or electric mover, and may be powered by any source, such as electricity from a generator, battery, wind turbine, or a solar panel. The term "mover" refers to any device which provides movement to part of the present invention. The gearbox provides for a choice of speeds, which can be selected for optimum biomass production. The mixing device may be connected to the motor and gearbox 2 by a shaft 3 of any useful length. The blades 4 may be made of any suitable material used in the bioprocessing art, and are of a size, quantity, and position sufficient to permit thorough and continuous mixing of the liquid microbial culture during processing. During operation, the mixing system portion of the present invention rotates and/or oscillates the blades to thoroughly and completely mix the microbial culture, and, as explained in more detail below, expose the microbial culture to the optimum amount of light.

The photobioreactor of the present invention also includes a lighting system to provide light to the microbial culture. The lighting system used in the present invention includes a light source located outside the tank, a light emitting device 6 mounted on the blades of the mixing device and/or connected to the shaft of the mixing device and/or mounted on a oscillating device; and a conduit 5 that transfers light from the light source to the light emitting device. In conjunction with the mixing system described above, the light emitting devices and conduit rotates and/or oscillates to provide necessary light and nutrients throughout the entire volume of the photobioreactor.

The speed of the rotating or oscillating system should be in a range that allows healthy growth of algae, and does not damage the cells. Suitable speeds can be determined by the survivability and/or growth rate for each species under specific conditions, and can be easily determined by one of skill in the art.

The light source may be any source of light known in the bioprocessing art. Examples of useful sources of light for use with the present invention include natural light sources such as sunlight, or artificial sources of light, such as lamps, bulbs, diffusion rods, LEDs, optical cable, and the like. The intensity and spectrum (wavelength) of the light can be determined based on the species of algae, and the amount of light necessary for photosynthesis processes throughout the entire volume of the photobioreactor. The light source may be powered by electricity and/or from conventional known generators or batteries, solar panels, wind turbine, and the like. In one embodiment, the source of light can be one or more mirrors 7, 8 which reflect sunlight directly to the photobioreactor through an optical conduit 5. Such mirrors can be installed near the photobioreactor (e.g., element 7) or at a distance from the photobioreactor (element 8) which allows for collection and transfer of any necessary amount of light. In an alternative embodiment, solar panels 13 may be used to transfer sun energy into current which is fed to light emitting devices through a conduit. In preferred embodiments, solar energy would be used by (1) collection and direct transfer to the photobioreactor in the form of light, or (2) conversion into electrical current (e.g., via solar panels) and subsequent transformation back into light by a light-emitting device.

In an alternative embodiment, light emitting devices and mixing device such as blades can be made as one unit: light-emitting mixing blades. For example, light emitting devices can be installed inside of light-transparent pipes or tubing that are attached to the shafts described above. In this alternative embodiment, these pipes or tubes function as the blades in the rotating system, mixing and illuminating the contents of the tank as described above. The tubes containing the light emitting devices may be of any shape or construction. Preferably, the tubes are blade-shaped and made of sufficiently strong material to withstand the forces involved in mixing the microbial culture. The same light sources as described above can be used in this alternative embodiment. To prevent algae from sticking to the interior parts of the devices, these components can be coated with a non-stick coating, such as PTFE, Teflon, and the like, or the materials used in the construction of the components may be made of materials such as polypropylene, polyethylene, quartz, and the like.

The amount of light required to sustain optimum algae growth will depend on a number of factors, such as algae species, concentration of algae in the mix, the size of the container, the intensity of the light source, and the like. These values can be determined by the user without undue experimentation. In addition, the speed of rotation and/or vibration is preferably a value that is below the shear value of the algae (e.g., the rotation or vibration rate which causes harm to the algae). The amount of light necessary for photosynthesis processes and amount of nutrients for growing algae cells will determine the speed of rotation or oscillation and intensity of light emitted by the light emitting devices.

Preferably, the rotational and/or oscillation speed should be in the range of 0.25 RPM up to an RPM that provides enough light for photosynthetic processes occurring throughout the tank, but does not harm the algae.

A conduit is employed to transfer light or current from the light source to the interior of the tank. One end of the conduit may be connected to a collector 9 to more efficiently collect light from the light source. The other end of the conduit may be connected to another collector 10 from which sunlight can be transferred to conduits inside the photobioreactor. Such conduits inside the photobioreactor collect the sunlight or current from this collector 10 in the process of rotating or oscillating with the mixing system. In preferred embodiments, optical cable is used as the conduit. Optical cable can also used as a light emitting device to deliver light to the photobioreactor.

Light emitting devices are mounted on the blades and/or connected to the shaft and/or mounted on an oscillating device inside the tank to distribute light throughout the mixing and/or oscillating microbial culture during processing. Any type of light emitting device may be used, including, but not limited to lamps, bulbs such as bulbs containing fluorescent or phosphorescent compounds, diffusion rods, LEDs, optical cable, and the like. Additionally, the blades may include a glowing or fluorescent or phosphorescent coating or may be hollow and contain a glowing or fluorescent or phosphorescent compound that can function as the light emitting device. In one embodiment, the blades themselves are hollow and filled with a glowing fluorescent or phosphorescent material. Additionally, the light emitting device may be lamps, bulbs including fluorescent and/or phosphorescent, diffusion rods, LEDs, optical cable, and the like, and can be used for lighting houses, building, construction, highways and like, using as a source of light a sun light or other sources. During operation of the photobioreactor of the present invention, the mixing system portion mixes the microbial culture so that nutrients including sewage, carbon dioxide, and the like, are readily available throughout the photobioreactor tank. Simultaneously, the lighting system mounted inside the tank provides continuous lighting to the mixing culture so that optimum growth of the culture is achieved. When the life cycle of the microbial culture is completed or the desired level of growth is achieved, the cells can be collected as a biomass, which consists of proteins, carbohydrates, and lipids.

The photobioreactor of the present invention may include a system for production of carbon dioxide which is necessary for photosynthesis processes. The carbon dioxide can be obtained from a variety of sources. For example, in process of production of ethanol by fermentation, carbon dioxide (CO2) will be produced. The produced CO2 can be transferred back to photobioreactor and used for photosynthetic processes in the photobioreactor and provide additional mixing of the microbial culture so that nutrients, carbon dioxide, and the like, are readily available throughout the photobioreactor tank.

In one embodiment carbon dioxide can be produced by burning different carbohydrates such as cellulose, glucose and the like:

$$C_6H_{12}O_6 + 6O_2 \rightarrow 6CO_2 + 6H_2O + \text{Heat}$$

As can be seen from this reaction, one molecule of $C_6H_{12}O_6$ produce 6 molecules of carbon dioxide, requires 6 molecules of oxygen and releases large amounts of heat. So, by burning cellulose and like carbohydrates, several things can be achieved:

a. Producing an amount of carbon dioxide necessary for photosynthesis processes;

b. Carbon dioxide can be produced in any burning device such as a furnace;

c. Removal of excess oxygen which develops in the process of growing algae and using this oxygen for burning cellulose and the like;

d. Released heat can be used for drying Algae Biomass.

The photobioreactor of the present invention may optionally include a harvesting system as shown in FIG. 2, where like components are designated by like numerals. In one embodiment shown in FIG. 2, the harvesting system may consist of a separating system 11 and a discharge system 12. The separating system should separate the biomass from the liquid microbial culture and also accelerate development of biomass. The separating system 11 can consist of filters, ultrasound devices, centrifuges, and the like. As shown in FIGS. 2 and 3, the discharge system includes blades or filters to separate and isolate the formed biomass. As mentioned above, the biomass itself is useful because it contains desirable amounts of proteins, carbohydrates, and lipids. These components may be used for a wide variety of applications. For example, lipids derived from the biomass may be used in the production of biodiesel fuel, carbohydrates derived from the biomass may be used in the production of ethanol, and proteins derived from the biomass may be used as food.

In alternative embodiments, movement of the tank can function as a mixer for the microbial culture. In such embodiments, panels or rotating pipes act as the tank portion of the present invention.

In one embodiment, space for growing microbial culture can be provided by panels. In such an embodiment, panels can be created by two flat sheets from glass and/or plastics transparent to light and/or any other materials and closed at the edge creating a close container. The distance between two sheets should provide enough space for growing microbial culture. The panels can be of any size or shape, and can be placed one on another to create a very large volume for growing of microbial culture.

Mixing of system of panels can be provided by hydraulic or pneumatic systems which will move one side of the panel up and down providing mixture of the liquid microbial culture. As a source of light can be sets of mirrors which reflects sun lights directly to photobioreactor and/or through conduits, as described above. These mirrors can be installed near and/or at distance from photobioreactor. As a conduit can be used optical cables which are connected a light emitting device. These light emitting devices described above are placed inside panels.

In an alternative embodiment, rotating pipes may be used in conjunction with the present photobioreactor. Use of pipes permits the tank portion to be constructed in a "modular" design, such that sections of tank are connected together to form a tank with a total desired volume. Space for growing microbial culture can be provided by pipes which are preferably light transparent. The diameters of the pipes should be of sufficient size to provide space for growing microbial culture. Several pipes can be put together to achieve any desired length, and can be placed horizontally and/or at any angle. The pipes or system of pipes can be rotated to provide thorough mixing of the microbial culture so that light and nutrients are optimized for metabolism.

In the case of one pipe, it is installed in way that it can be rotated around axis perpendicular to the pipe in the middle of the pipe, so that it turns end-over-end. In this case, a turn of 180 degrees turns pipe upside down to mix the microbial culture and nutrients. During rotation all sides of pipe will be exposed to sunlight or other light sources described above. In the case of pipes, a source of light can be sets of mirrors which reflects sun lights directly to photobioreactor and/or through conduits, as described above. These mirrors can be installed near and/or at distance from photobioreactor. As a conduit can be used optical cables which are connected a light emitting device. These light emitting devices are placed inside panels.

To provide increase efficiencies in producing algae in open bodies of water such as ponds, raceways, or pools, the mixing system and lighting system of the photobioreactor of the present invention may be mounted on a framework. The framework may be mobile (e.g., mounted on a wheeled cart) so that the mixing and lighting system may be moved to various places in the open water body through a network of tracks that may be installed in the pond. The framework may take any desired shape, and may be made of any suitable materials.

The photobioreactor of the present invention may be used to produce a variety of materials including biodiesel fuel, ethanol, and protein. To produce biodiesel fuel, ethanol, or protein using the photobioreactor of the present invention, the photobioreactor is used to generate a biomass derived from a liquid microbial culture such as algae. The lipid portion of the biomass may be separated and used to produce biodiesel fuel using known transesterification processes. Alternatively, to produce ethanol, the carbohydrate portion of the biomass is separated and used in fermentation processes to produce ethanol.

In process of production of ethanol, carbon dioxide ($CO_2$) will be produced. The produced $CO_2$ will be used for photosynthetic processes in the photobioreactor and provide additional mixing of the microbial culture so that nutrients, carbon dioxide, and the like, are readily available throughout the photobioreactor tank Production of biodiesel fuel or ethanol may be done in a continuous process using a continuous processor described below in this application. Biomass from the photobioreactor of the present invention is moving to extraction devices where lipids and carbohydrates are derived. After lipids and carbohydrates move to a continuous processor.

Production of biodiesel fuel or ethanol may be done batchwise, or may be done in a continuous process using a continuous processor attached to the photobioreactor of the present invention. A continuous processor consists of sections where each section is a processor with the same functionality as all section together. Each section of processor consists of cylinders such as pipes which can be connected one to another. Blades may be installed in each pipe to mix and move ingredients through the pipe in a continuous process. Blades can be different type such as impellers, propellers, Jiffy mixers or any other types. These blades can be installed on the shaft inside the cylinders where one end of the shaft is connected to a gear box and motor, and another end of the shaft placed on support and can be connected to the shaft from another section. The shaft can be installed from a side of the cylinder. In this case one side of the shaft connects to the motor this gear box. On the other side, which locates inside of the cylinder, are placed the blades.

To complete the transesterification or fermentation processes, all ingredients should be mixed for certain amounts of time. To increase mixing time for the same productivity or increase production capacity for the same mixing time, the length of the processor may be varied by adding or subtracting sections.

Production of ethanol fuel may be done in a continuous process using a continuous processor attached to the photobioreactor of the present invention. The process of production ethanol consist of several processes including fermentation. In the process of production ethanol, carbon dioxide will be produced. As described above, this carbon dioxide can be transferred back to the photobioreactor and can be used by algae for photosynthesis processes.

EXAMPLES

Example 1

Photobioreactors with Rotating Light Emitting Devices

A photobioreactor was constructed as shown in FIG. 2. The tank portion for containing algae and carbon dioxide had a rectangular shape and was constructed as a continuous photobioreactor. The tank contained *Scenedesmus dimorphus* algae along with Bold's Basic Medium consisting of (for 400 ml) 10 g $NaNO_3$, 2 g $MgSO_4.7H_2O$, 4 g $K_2HPO_4$, 6 g $KH_2PO_4$, 1 g $CaCl_2$, and 1 g NaCl.

The rotating mixing system contained within the tank included motors with a gearbox in mechanical communication with shafts. The motor and gearbox was run at a speed of about 1.0 RPM. Rotating blades made from Plexiglas tubing were mounted on the shafts, with fluorescent bulbs installed inside these tubes. The rotating blades were capable of mixing all liquid microbial culture throughout the entire volume of the tank.

The lighting system included mirrors and solar panels to collect sunlight, and a light emitting device mounted inside the tubing so that during rotation of the blades, the entire volume of the tank is exposed to light. A conduit was used to transfer the light from the collection source to the light emitting device.

As discussed above, the amount of light necessary for photosynthesis processes and amount of nutrients for growing Algae cells will determine the speed of rotation and intensity of light emitting devices.

Example 2

Photobioreactors with Oscillating Light Emitting Devices

A photobioreactor was constructed as shown in FIG. 3. The tank portion for containing algae and carbon dioxide was constructed of Plexiglas and had a rectangular shape (72 inches in length, 14.5 inches in width, and 16 inches in height, wall thickness was ¼ inch). Ribs were added to the tank for reinforcement. The tank contained *Scenedesmus dimorphus* algae along with Bold's Basic Medium consisting of (for 400 ml) 10 g $NaNO_3$, 2 g $MgSO_4.7H_2O$, 4 g $K_2HPO_4$, 6 g $KH_2PO_4$, 1 g $CaCl_2$, and 1 g NaCl.

The oscillating mixing system included motors and gearboxes in mechanical communication with the frame system, and blades mounted on the frame system. In operation, the blades were capable of mixing all the culture throughout the entire volume of the tank.

The frame system included a fixed frame that supported an oscillating frame, a horizontally oscillating frame with a cleaning layer, and vertical oscillating frames including blades and light emitting devices.

The lighting system included a system similar to that described in Example 1.

A harvesting system was also included. The tank is constructed as continuous photobioreactor where a liquid microbial culture such as Algae should grow in the continuous photobioreactor for certain amount of time for certain species. This time will determine speed of the movement of Algae and length of the continuous photobioreactor.

The tank is placed on a support system 17 that can withstand the weight of a tank which contains a liquid microbial culture. During operation, the horizontal oscillating frame 20 moves forward and backward against the fixed frame 18 in a rocking motion. The speed of the motor is about 1.0 RPM.

A cleaning layer 14 is attached to the horizontal moving frame and includes holes with shape and size equal to the shape and size of the blades. These blades consist of pipes (tubing) with the inserted light emitting devices. This pipe is transparent to light. The vertical moving frame 19 can also move up and down against the horizontal moving frame. Movement of the vertical frame is provided by a motor and gearbox mounted on the horizontal frame and operating at a speed of about 5 RPM. Pipes with inserted light emitting devices are mounted on the vertical moving frame which also partially insert in holes of the cleaning layer. In operation, when the light emitting devices move up and down against the cleaning layer, built up algae is removed. The amount of light necessary for photosynthesis processes and amount of nutrients for growing Algae cells will determine the speed of rotation and intensity of light emitting devices.

What is claimed is:

1. A photobioreactor comprising:
A) a tank for containing a liquid microbial culture;
B) a rotating sunlight-propagating system comprising:
(1) a rotating system comprising:
one or more motors with one or more shafts connected to and driven by said motors;
(2) a sunlight-propagating system comprising:
(a) sunlight as a source of light;
(b) one or more light-transparent pipes, tubing, which have a closed end to prevent penetration of the culture inside the pipes and tubing, connected to the shafts and driven by motors;
wherein said sunlight propagates through all and any lengths of the light-transparent pipes, tubing and therefore can reach any spot of the photobioreactor; and
sunlight from the inside of the pipes propagates through the light-transparent wall and the end surfaces of the pipes through all thicknesses of the microbial culture;
(c) a conduit that transfers sunlight to light-transparent pipes, tubing; and said motor or motors rotate the sunlight-propagating system through the entire microbial culture with a speed which allows distribution of sunlight to all cells of the microbial culture throughout the entire volume of the tank in amounts which will provide optimum growth.

2. The photobioreactor of claim 1, wherein said liquid microbial culture comprises algae, nutrients, and carbon dioxide.

3. The photobioreactor of claim 1, wherein said motor is an electric motor, a pneumatic motor.

4. The photobioreactor of claim 1, wherein said conduit is optical pipes, tubing.

5. The photobioreactor of claim 1, wherein said tank is made from a modular or continuous design.

6. The photobioreactor of claim 1, wherein said lighting system further comprises mirrors and collection devices to collect sunlight and provide it directly to a rotating sunlight-propagating system.

7. A photobioreactor comprising:
A) a tank for containing a liquid microbial culture;
B) a rotating light-delivery system comprising:
1) a rotating system comprising:
at least one motor, at least one shaft connected to and driven by said motor;
2) a light-propagating system comprising:
(a) source(s) of light whose light is propagated inside of light-transparent pipes, tubing and can be located outside and/or at any part of the pipes to provide distribution of the light;
one or more light-transparent pipes, tubing, which have a closed end to prevent penetration of culture inside the pipes and are connected to the shafts and driven by the motors;
wherein said light propagates through all and any lengths of the light-transparent pipes, tubing and therefore can reach any spot of the photobioreactor;
and light from the inside of the pipes propagates through the transparent wall and the end surfaces of the pipes, tubing through all thicknesses of the microbial culture;
and said motor or motors rotate sunlight-propagating system through the entire microbial culture with a speed which allows distribution of sunlight to all cells of the microbial culture throughout the entire volume of the tank in amounts which will provide optimum growth.

8. The photobioreactor of claim 7, wherein said liquid microbial culture comprises algae, nutrients, and carbon dioxide.

9. The photobioreactor of claim 7, wherein said motor is an electric motor, a pneumatic motor.

10. The photobioreactor of claim 7, wherein said light source is sunlight or an artificial source powered by electricity.

11. The photobioreactor of claim 7, wherein said light source is selected from the group consisting of lamps, bulbs, diffusion rods, LEDs, optical cables, fluorescent compounds, phosphorescent compounds, and combinations thereof.

12. The photobioreactor of claim 7, wherein said tank is made from a modular or continuous design.

13. The photobioreactor of claim 7, wherein said lighting system further comprises mirrors and collection devices to collect light and provide it directly to a rotating light-propagating system.

14. A photobioreactor comprising:
A) a tank for containing a liquid microbial culture;
B) an oscillating sunlight-propagating system comprising:
(1) an oscillating system comprising:
(a) one or more oscillating motors;
(b) a frame system comprising one or more oscillating frames, which are connected to said oscillating motors;
(2) a sunlight-propagating system comprising:
(a) sunlight as a source of light;
(b) one or more light-transparent pipes, tubing, which each have a closed end to prevent penetration of the culture inside the pipes, tubing, connected to oscillating frames and driven by oscillating motors;
wherein sunlight propagates through all and any length of the pipes, and therefore can reach all and any spots of the photobioreactor;
and sunlight from the inside of the pipes propagates through the wall and the ends of the pipes and/or tubing through all thicknesses of the microbial culture;
(c) a conduit which transfers sunlight to light-transparent pipes, tubing and said motor or motors oscillate the sunlight-propagating system through the entire microbial culture with a speed which allows distribution of sunlight to all cells of the microbial culture throughout the entire volume of the tank in amounts which will provide optimum growth.

15. The photobioreactor of claim 14 wherein said liquid microbial culture comprises algae, nutrients, and carbon dioxide.

16. The photobioreactor of claim 14, wherein said conduit is optical pipes, tubing.

17. The photobioreactor of claim 14, wherein said tank is made from a modular or continuous design.

18. The photobioreactor of claim 14, wherein said lighting system further comprises mirrors and collection devices to collect light and provide it directly to an oscillating sunlight-propagating system.

19. A photobioreactor comprising:
A) a tank for containing a liquid microbial culture;
B) an oscillating light-propagating system comprising:
(1) an oscillating system comprising:
(a) one or more oscillating motors;
(b) a frame system comprising one or more oscillating frames connected to and driven by oscillating motors;
(2) a light-propagating system comprising:
(a) source(s) of light whose light is propagated inside of light-transparent pipes, tubing and can be located outside and/or at any part of the pipes, tubing to provide optimum distribution of the light;
(b) one or more light-transparent pipes, tubing, which have a closed end to prevent penetration of the culture inside the pipes, tubing, connected to the oscillating frames;
wherein said light propagates through all and any lengths of the light-transparent pipes, tubing and therefore can reach any spot of the photobioreactor;
and light from the inside of the pipes, tubing propagates through the transparent wall and the end surfaces of the pipes through all thicknesses of the microbial culture;
and said motors oscillate the sunlight-propagating system through the entire microbial culture with a speed which allows distribution of sunlight to all cells of the microbial culture throughout the entire volume of the tank in amounts which will provide optimum growth.

20. The photobioreactor of claim 19, wherein said liquid microbial culture comprises algae, nutrients, and carbon dioxide.

21. The photobioreactor of claim 19, wherein said light source is sunlight or an artificial source powered by electricity.

22. The photobioreactor of claim 19, wherein said light source is selected from the group consisting of lamps, bulbs, diffusion rods, LEDs, optical cables, fluorescent compounds, phosphorescent compounds, and combinations thereof.

23. The photobioreactor of claim 19, wherein said tank is made from a modular or continuous design.

24. The photobioreactor of claim 19, wherein said lighting system further comprises mirrors and collection devices to collect light and provide it directly to an oscillating light-propagating system.

25. A photobioreactor, comprising:
A) a body of water, containing a liquid microbial culture;
B) a mobile framework which moves to all areas of the body of water and/or can be located at certain areas;
C) a rotating sunlight-propagating system, which is attached to a mobile framework, comprising:
1. A rotating system comprising:
one or more motors with one or more shafts connected to and driven by the motors;
2. A sunlight-propagating system comprising:
(a) sunlight as a source of light;
(b) one or more light-transparent pipes, tubing, which have a closed end to prevent penetration of the culture inside the pipes, tubing, connected to the shafts and driven by the motors;
wherein said sunlight propagates through all and any lengths of the light-transparent pipes, tubing and therefore can reach any spot of the body of water;
and sunlight from the inside of the pipes propagates through the light-transparent wall and the end surfaces of the pipes through all thicknesses of the microbial culture;
(c) a conduit that transfers sunlight to light-transparent pipes, tubing and said motor or motors rotate sunlight-propagating system through the microbial culture with a speed which allows distribution of sunlight to all cells of the microbial culture throughout the entire volume of the body of water in amounts which will provide optimum growth.

26. A photobioreactor, comprising:
A) a body of water containing a liquid microbial culture;
B) a mobile framework which moves to all areas of body of water or can be located at certain areas;

C) an oscillating sunlight-propagating system, which is attached to a mobile framework, comprising:
  (1) an oscillating system comprising:
    (a) one or more oscillating motors;
    (b) a frame system comprising of one or more oscillating frames, which are connected to and driven by oscillating motors;
  (2) a sunlight-propagating system comprising:
(a) sunlight as a source of light;
(b) one or more light-transparent pipes, tubing which each have a closed end to prevent penetration of culture inside the pipes, tubing, connected to and driven by oscillating frames;
  wherein sunlight propagates through all and any length of the pipes, and therefore can reach all and any spots of the photobioreactor;
  and sunlight from the inside of the pipes propagates through the wall and the end surfaces of the pipes and/or through all thicknesses of microbial culture;
(c) a conduit which transfers sunlight to light-transparent pipes, tubing and said motor or motors oscillates sunlight-propagating system through the entire microbial culture with a speed which allows distribution of sunlight to all cells of the microbial culture throughout the entire volume of the body of water in amounts which will provide optimum growth.

* * * * *